United States Patent [19]

Narbeshuber et al.

[11] Patent Number: 6,043,189
[45] Date of Patent: Mar. 28, 2000

[54] CATALYST FOR SIDE-CHAIN ALKYLATION

[75] Inventors: Thomas Narbeshuber, Ludwigshafen; Michael Trefzer, Otterstadt; Eugen Gehrer, Ludwigshafen, all of Germany

[73] Assignee: BASF Aktiengesellschaft, Ludwigshafen, Germany

[21] Appl. No.: 09/151,811

[22] Filed: Sep. 14, 1998

[30] Foreign Application Priority Data

Sep. 15, 1997 [DE] Germany ............................ 197 40 539

[51] Int. Cl.[7] ..................................... B01J 23/02
[52] U.S. Cl. ........................ 502/344; 502/340; 502/349
[58] Field of Search ................................... 502/340, 344, 502/349

[56] References Cited

FOREIGN PATENT DOCUMENTS

| | | |
|---|---|---|
| 0 575 724 | 4/1993 | European Pat. Off. ........ C07C 15/40 |
| 558 941 | 9/1993 | European Pat. Off. . |
| 575 724 | 12/1993 | European Pat. Off. . |
| 446 896 | 12/1994 | European Pat. Off. . |
| 636 597 | 2/1995 | European Pat. Off. . |
| 0 558 941 | 5/1996 | European Pat. Off. ........ C07C 15/40 |
| 902 043 | 4/1960 | United Kingdom . |

*Primary Examiner*—John F. Niebling
*Assistant Examiner*—Alexander G. Ghyka
*Attorney, Agent, or Firm*—Keil & Weinkauf

[57] ABSTRACT

The catalyst comprises at least one alkali metal on a doped carrier, where the doped carrier can be prepared from at least one zirconium and/or alkaline earth metal compound as carrier and at least one alkali metal compound as dopant and calcining the doped carrier at 350° C. or below, the alkali metal/carrier ratio by weight being from 0.01 to 5 and the dopant/carrier ratio by weight being from 0.01 to 5.

6 Claims, No Drawings

CATALYST FOR SIDE-CHAIN ALKYLATION

The invention relates to a catalyst, to its use in reactions catalyzed by strong bases, and to a process for side-chain alkylation or side-chain alkenylation of alkylaromatic or alkylalicyclic compounds with olefins or diolefins.

Side-chain alkylation or alkenylation, especially of aromatic compounds which have an acidic proton in the α position of the side chain, in the presence of catalysts is known.

GB-B-902,043 describes a supported alkali metal catalyst. The catalyst consists of an alkali metal on magnesium oxide, calcium oxide, zinc oxide or barium oxide as carrier. The doped carrier is calcined and then heated to 300° C. with the alkali metal while stirring under an inert atmosphere. The catalyst is employed, for example, for side-chain alkylation of toluene with ethene or propene.

EP-B-0 446 896 relates to a process for preparing alkyl-substituted aromatic hydrocarbons. The catalysts employed are metallic sodium or potassium supported on magnesium oxide or calcium oxide. The magnesium oxide or calcium oxide in this case contains water and is prepared by calcining an appropriate oxide or hydroxide. The water content is adjusted by the manner of carrying out the calcination. In this connection, a carrier is regarded as anhydrous if it has been calcined at 800° C. The catalysts are employed, for example, for side-chain alkylation of toluene with ethene to give isopropylbenzene.

EP-B-0 575 724 discloses the use of a catalyst which is prepared by impregnating zirconium oxide powder with potassium hydroxide solution, subsequently calcining in air at 500° C. and applying metallic sodium to the carrier. The catalyst is employed for side-chain alkenylation of toluene with butadiene.

EP-B-0 558 941 discloses the use of a catalyst which is prepared by impregnating magnesium oxide powder with an aqueous solution of potassium carbonate or potassium hydroxide, calcining in air at 500° C. and applying metallic sodium. The catalyst is employed for side-chain alkenylation of xylene or ethylbenzene with butadiene.

EP-A-0 636 597 describes a process for side-chain alkenylation of o-xylene with butadiene using as catalyst aluminum oxide, calcium oxide or zirconium oxide, which is impregnated with aqueous KOH and has then been calcined at from 500 to 550° C. The carrier is coated with metallic sodium.

The known catalysts generally have high selectivity. However, the catalytic activity, which is evident from the conversions which can be achieved, is still too low in many cases. In addition, for the known catalysts it is necessary to calcine the materials at about 500° C. in order to obtain sufficient activity and selectivity of the catalysts. A preparation process of this type is costly.

It is an object of the present invention to provide a catalyst for side-chain alkylation or side-chain alkenylation which avoids the disadvantages of known catalysts and, besides high selectivity, has a high activity and long useful life and can be prepared at low cost.

We have found that this object is achieved by providing a catalyst comprising at least one alkali metal on a doped carrier, where the doped carrier can be prepared from at least one zirconium and/or alkaline earth metal compound as carrier and at least one alkali metal compound as dopant and calcining the doped carrier at 350° C. or below, the alkali metal/carrier ratio by weight being from 0.01 to 5 and the dopant/carrier ratio by weight being from 0.01 to 5. The object is also achieved by using this catalyst in reactions catalyzed by strong bases, preferably for side-chain alkylation or side-chain alkenylation of alkylaromatic or alkylalicyclic compounds with olefins or diolefins, for double-bond isomerization of olefins or for dimerization of olefins.

The object is further achieved by providing a process for side-chain alkylation or side-chain alkenylation of alkylaromatic or alkylalicyclic compounds by reacting with olefins or diolefins, the reaction being carried out in the presence of a catalyst defined above.

It has been found according to the invention that, in particular, catalysts based on zirconium and/or alkaline earth metal oxides as carriers which are doped with alkali metal compounds show a distinctly higher activity and thus a distinctly improved conversion when they have been calcined at 350° C. or below, preferably from 250 to 300° C., particularly preferably from 250 to 285° C.

The alkali metal/carrier ratio in the catalyst according to the invention is preferably from 0.01 to 2, particularly preferably from 0.01 to 1. The alkali metal in this case is preferably sodium or potassium, in particular sodium. It is also possible to employ mixtures of alkali metals.

The alkali metal is present on a doped carrier which can be prepared and is preferably prepared by mixing, in particular mixing intimately, at least one zirconium and/or alkaline earth metal compound as carrier with at least one alkali metal compound as dopant and calcining the doped carrier at the temperatures stated above.

The doped carrier is preferably prepared by mixing aqueous solutions and precipitating the doped carrier, mixing the powdered components or impregnating the solid carrier with an aqueous solution of the dopant. It is possible in this connection to employ all suitable zirconium, alkaline earth metal and alkali metal compounds which can be converted in the calcination preferably into the oxide form. Moreover the doped carrier is preferably prepared from oxides, hydroxides and/or halides as carrier and dopant.

The zirconium, alkaline earth metal and/or alkali metal compounds can be employed, for example, in the form of solutions in any suitable solvents, preferably aqueous solvents, in particular as aqueous solutions.

The doped carrier is preferably prepared by impregnating a powder, a paste or a suspension of at least one zirconium and/or alkaline earth metal hydroxide as carrier with an aqueous solution of at least one alkali metal hydroxide and/or carbonate as dopant, drying and then calcining.

The carrier in this case is preferably selected from compounds of zirconium and/or magnesium. The dopant is preferably selected from potassium compounds, particularly preferably potassium hydroxide or potassium carbonate. Potassium hydroxide or potassium carbonate is particularly preferably employed.

It is preferred for a powder or a paste of zirconium tetrahydroxide or magnesium hydroxide as carrier to be impregnated with an aqueous solution of potassium carbonate ($K_2CO_3$) or potassium hydroxide (KOH) as dopant. The alkali metal preferably applied in this case is sodium.

Preparation of the Catalysts

The catalysts are prepared by (a) mixing, in particular mixing intimately, at least one zirconium and/or alkaline earth metal compound as carrier with at least one alkali metal compound as dopant, where appropriate drying the doped carrier, (b) calcining the doped carrier obtained in this way and (c) applying at least one alkali metal to the calcined doped carrier by applying the molten alkali metal to the carrier, or impregnating the carrier with solutions of an alkali metal azide, drying the carrier and decomposing the alkali metal azide, or vapor-deposition of the alkali metal on the carrier, or impregnating the carrier with ammoniacal solutions of the alkali metal and removing the ammonia.

Mixing powders, pastes or suspensions for this purpose can take place with known equipment, for example kneaders or stirrers.

When aqueous solutions of the components are used, the water is preferably removed from the doped carrier by drying before the calcination. Calcination is also possible without previous drying, in which case the (aqueous) solvent escapes at the start of the calcination.

The doped carrier can be calcined under reduced pressure, under atmospheric pressure or under elevated pressure. It can moreover take place either in an oxygen-containing atmosphere or in an inert gas-atmosphere, such as under helium, nitrogen or argon, or under a reactive gas atmosphere, such as under hydrogen, ammonia, carbon dioxide or carbon monoxide.

The alkali metals are applied to the calcined and doped carriers in a manner known per se. This includes application to the carrier in the molten state at from 100 to 300° C., as described, for example, in GB-A-1 143 993. For this purpose, the appropriate amount of the alkali metal is added as extrudate or block to the carrier and mixed with it while heating. During this, the alkali metal is dispersed finely on the carrier. It is furthermore possible to prepare the alkali metals by impregnating with solutions of the alkali metal azides, followed by thermal decomposition of the azides. A corresponding process is described, for example, in FR-A-2 609 024. The alkali metals can also be applied to the carrier by vapor deposition. This generally takes placed under reduced pressure.

The carriers can furthermore be impregnated with ammoniacal solutions of the alkali metals, and the ammonia can then be evaporated. The application of the alkali metals to the carrier moreover preferably takes place under reduced pressure or under an inert gas atmosphere, such as under helium, nitrogen, hydrogen or argon.

The catalysts are employed in reactions catalyzed by strong bases, preferably for side-chain alkylation or side-chain alkenylation of alkylaromatic or alkylalicyclic compounds with olefins or diolefins, for double-bond isomerization of olefins or for dimerization of olefins.

The reaction in this case is generally carried out at from $-50$ to $400°$ C., preferably from $-20$ to $300°$ C., particularly preferably 80 to $250°$ C., especially 100 to $220°$ C., under a pressure of, preferably, 0.1 to 200, particularly preferably 1 to 150, especially 1 to 100, bar.

All suitable alkylaromatic compounds can be employed for this purpose. They may have as aromatic nucleus for example a benzene or naphthalene nucleus. Also suitable are alkylalicyclic compounds in which the cyclic nucleus may be a cyclic alkyl, alkenyl or alkynyl radical. It is also possible to employ radicals in which a plurality of ring structures are connected together. The ring structures have an acidic hydrogen atom in the α position of the side chain. They preferably have at least one alkyl radical which is bonded to the cyclic structure. The alkyl radicals may in this connection have any length and be substituted by other substituents. The alkylaromatic compounds preferably employed are benzenes substituted by 1 to 6, preferably 1 to 3, especially 1 to 2, $C_{1-20}$-, preferably $C_{1-3}$-alkyl radicals, and naphthalenes substituted by 1 to 10, preferably 1 to 5, particularly preferably 1 to 2, $C_{1-20}$-, preferably $C_{1-3}$-alkyl radicals, and the alkylalicyclic compounds preferably employed are cyclopentenes or cyclohexenes respectively substituted by 1 to 5, preferably 1 or 2, or by 1 to 6, preferably 1 to 3, in particular 1 or 2, $C_{1-20}$-, preferably $C_{1-3}$-alkyl radicals.

The olefins for the alkylation preferably have 2 to 20, particularly preferably 2 to 10, especially 2 to 5, carbon atoms. Ethene, propene, 1-butene, 2-butene, isobutene, 1-pentene, 2-pentene, 2-methyl-1-butene, 2-methyl-2-butene and/or 3-methyl-1-butene are preferably employed. Ethene and propene are particularly preferred. The diolefins for the alkenylation preferably have 4 to 20, particularly preferably 4 to 10, especially 4 to 6, carbon atoms. Butadiene and/or isoprene are particularly preferably employed.

Particularly preferred reactions are those of toluene with ethene or propene to give propylbenzene or isobutylbenzene, that of cumene with ethene to give tert-amylbenzene and those xylenes with butadiene to give 5-tolylpentenes.

The reaction can be carried out batchwise or, preferably, continuously in the liquid or gas phase, preferably in the liquid phase. Known equipment can moreover be employed for carrying out the process.

The invention is explained in detail by means of examples hereinafter.

EXAMPLES

Preparation Examples

Catalyst A:

$Mg(OH)_2$ powder (Merck) was impregnated with 10% by weight KOH (dissolved in $H_2O$). The suspension was evaporated to dryness, and the resulting powder was calcined in a stream of air at 500° C. for 16 h. The material was then stirred dry at 280° C. under reduced pressure for 3 h. 10% by weight metallic sodium were added to this powder and dispersed at 280° C.

Catalyst B:

$Mg(OH)_2$ powder (Merck) was impregnated with 10% by weight KOH (dissolved in $H_2O$). The suspension was evaporated to dryness, and the resulting powder was calcined in a stream of air at 250° C. for 16 h. The material was then stirred dry at 250° C. under reduced pressure for 3 h. 10% by weight metallic sodium were added to this powder and dispersed at 250° C.

Catalyst C:

$Mg(OH)_2$ powder (Merck) was impregnated with 68% by weight $K_2CO_3$ (dissolved in $H_2O$). The suspension was evaporated to dryness, and the resulting powder was calcined in a stream of air at 500° C. for 16 h. The material was then stirred dry at 280° C. under reduced pressure for 3 h. 10% by weight metallic sodium were added to this powder and dispersed at 280° C.

Catalyst D:

$Mg(OH)_2$ powder (Merck) was impregnated with 68% by weight $K_2CO_3$ (dissolved in $H_2O$). The suspension was evaporated to dryness, and the resulting powder was calcined in a stream of air at 250° C. for 16 h. The material was then stirred dry at 250° C. under reduced pressure for 3 h. 10% by weight metallic sodium were added to this powder and dispersed at 250° C.

Catalyst E:

$Mg(OH)_2$ powder (Merck) was impregnated with 10% by weight KOH (dissolved in $H_2O$). The suspension was evaporated to dryness, and the resulting powder was calcined in a stream of air at 250° C. for 1 h. The material was then stirred dry at 250° C. under reduced pressure for 3 h. 10% by weight metallic sodium were added to this powder and dispersed at 250° C.

Catalyst F:

$Mg(OH)_2$ powder (Merck) was impregnated with 10% by weight KOH (dissolved in $H_2O$). The suspension was evaporated to dryness, and the resulting powder was calcined in a stream of air at 250° C. for 2 h. The material was then stirred dry at 250° C. under reduced pressure for 3 h. 10% by weight metallic sodium were added to this powder and dispersed at 250° C.

Catalyst G:

Mg(OH)$_2$ powder (Merck) was impregnated with 10% by weight KOH (dissolved in H$_2$O). The suspension was evaporated to dryness, and the resulting powder was calcined in a stream of air at 250° C. for 5 h. The material was then stirred dry at 250° C. under reduced pressure for 3 h. 10% by weight metallic sodium were added to this powder and dispersed at 250° C.

Catalyst H:

Zr(OH)$_4$ paste (BASF) was impregnated with 46% by weight KOH (dissolved in H$_2$O). The suspension was evaporated to dryness, and the resulting powder was calcined in a stream of air at 500° C. for 16 h. The material was then stirred dry at 280° C. under reduced pressure for 3 h. 10% by weight metallic sodium were added to this powder and dispersed at 280° C.

Catalyst I:

Zr(OH)$_4$ paste (BASF) was impregnated with 46% by weight KOH (dissolved in H$_2$O). The suspension was evaporated to dryness, and the resulting powder was calcined in a stream of air at 250° C. for 16 h. The material was then stirred dry at 250° C. under reduced pressure for 3 h. 10% by weight metallic sodium were added to this powder and dispersed at 250° C.

Examples 1 to 9

Catalysts A–I were mixed with 85 g of toluene in a pressure-resistant reaction vessel. 20 g of propene were added and then the reaction vessel was heated to 160° C., and the reaction suspension was stirred for 12 hours. 10 g of catalyst were used in each of Examples 1 to 8, and 6 g of catalyst were used in Example 9. The results are listed in Table 1.

TABLE 1

| Example | Cat. | $U_{Tol}$ | $U_{Prop}$ | $Y_{iBB(Tol)}$ | $Y_{iBB(Prop)}$ | $S_{iBB(Tol)}$ | $S_{iBB(Prop)}$ |
|---|---|---|---|---|---|---|---|
| 1 | A | 27.3% | 58.7% | 24.4% | 43.3% | 89.5% | 73.7% |
| 2 | B | 35.4% | 80.3% | 31.4% | 57.2% | 88.6% | 71.3% |
| 3 | C | 21.4% | 44.3% | 19.2% | 34.6% | 89.9% | 78.0% |
| 4 | D | 37.7% | 74.6% | 33.3% | 49.4% | 88.5% | 66.1% |
| 5 | E | 29.5% | 67.9% | 25.9% | 50.1% | 87.9% | 73.7% |
| 6 | F | 25.4% | 55.5% | 22.7% | 44.1% | 89.3% | 79.5% |
| 7 | G | 22.9% | 60.9% | 20.0% | 40.3% | 87.5% | 66.1% |
| 8 | H | 14.5% | 33.4% | 12.9% | 23.2% | 88.7% | 69.5% |
| 9 | I | 14.7% | 30.0% | 13.3% | 23.4% | 90.1% | 78.0% |

$U_{Tol}$ = Conversion based on toluene
$U_{prop}$ = Conversion based on propene
$Y_{iBB(Tol)}$ = Yield of isobutylbenzene based on toluene
$Y_{iBB(Prop)}$ = Yield of isobutylbenzene based on propene
$S_{iBB(Tol)}$ = Selectivity for isobutylbenzene based on toluene
$S_{iBB(Prop)}$ = Selectivity for isobutylbenzene based on propene

We claim:

1. A catalyst comprising at least one alkali metal on a doped carrier, where the doped carrier is prepared from at least one zirconium and/or alkaline earth metal compound as carrier and at least one alkali metal compound as dopant and the doped carrier is calcined at 350° C. or below, the alkali metal/carrier ratio by weight being from 0.01 to 5 and the dopant/carrier ratio by weight being from 0.01 to 5.

2. A catalyst as claimed in claim 1, wherein the doped carrier is prepared by mixing aqueous solutions of the components and precipitating the doped carrier, mixing the powdered components or impregnating the solid carrier with an aqueous solution of the dopant.

3. A catalyst as claimed in claim 1, wherein the doped carrier is prepared from oxides, hydroxides and/or halides as carrier and dopant.

4. A catalyst as claimed in claim 1, wherein the doped carrier is prepared by impregnating a powder, a paste or a suspension of at least one zirconium and/or alkaline earth metal hydroxide as carrier with an aqueous solution of at least one alkali metal hydroxide and/or carbonate as dopant, drying and then calcining.

5. A catalyst as claimed in claim 4, which is prepared by impregnating a powder or a paste of zirconium tetrahydroxide or magnesium hydroxide as carrier with an aqueous solution of K$_2$CO$_3$ or KOH as dopant, and applying sodium as alkali metal to the doped carrier.

6. A process for preparing a catalyst as claimed in claim 1, by (a) mixing, in particular mixing intimately, at least one zirconium and/or alkaline earth metal compound as carrier with at least one alkali metal compound as dopant, where appropriate drying the doped carrier, (b) calcining the doped carrier obtained in this way and (c) applying at least one alkali metal to the calcined doped carrier by applying the molten alkali metal to the carrier, or impregnating the carrier with solutions of an alkali metal azide, drying the carrier and decomposing the alkali metal azide, or vapor-deposition of the alkali metal on the carrier, or impregnating the carrier with ammoniacal solutions of the alkali metal and removing the ammonia.

* * * * *

UNITED STATES PATENT AND TRADEMARK OFFICE
CERTIFICATE OF CORRECTION

PATENT NO. : 6,043,189
DATED : March 28, 2000
INVENTOR(S) : Narbeshuber, et. al.

It is certified that error appears in the above-identified patent and that said Letters Patent is hereby corrected as shown below:

Column 6, claim 5, line 43, after "applying" delete "the".

Signed and Sealed this

Sixth Day of February, 2001

Attest:

Q. TODD DICKINSON

*Attesting Officer*  *Director of Patents and Trademarks*